US011273121B2

(12) United States Patent
Steinhorn et al.

(10) Patent No.: US 11,273,121 B2
(45) Date of Patent: Mar. 15, 2022

(54) MATRIX-METALLOPROTEINASE (MMP) INHIBITORY EXTRACT AND METHODS OF USE THEREOF

(71) Applicant: Comvita Limited, Te Puke (NZ)

(72) Inventors: Gregor Aaron Steinhorn, Te Puke (NZ); Sigrid Vorwerk, Te Puke (NZ)

(73) Assignee: Comvita Limited, Te Puke (NZ)

( * ) Notice: Subject to any disclaimer, the term of this patent is extended or adjusted under 35 U.S.C. 154(b) by 0 days.

(21) Appl. No.: 15/309,167

(22) PCT Filed: May 5, 2015

(86) PCT No.: PCT/NZ2015/000034
§ 371 (c)(1),
(2) Date: Nov. 4, 2016

(87) PCT Pub. No.: WO2015/170993
PCT Pub. Date: Nov. 12, 2015

(65) Prior Publication Data
US 2017/0071849 A1 Mar. 16, 2017

(30) Foreign Application Priority Data
May 6, 2014 (NZ) ........................... 624517

(51) Int. Cl.
| | | |
|---|---|---|
| A61K 8/98 | (2006.01) | |
| A61Q 19/08 | (2006.01) | |
| A61K 8/37 | (2006.01) | |
| A61K 35/644 | (2015.01) | |
| A61K 8/34 | (2006.01) | |

(52) U.S. Cl.
CPC ............... *A61K 8/988* (2013.01); *A61K 8/34* (2013.01); *A61K 8/37* (2013.01); *A61K 35/644* (2013.01); *A61Q 19/08* (2013.01); *A61K 2800/782* (2013.01); *A61K 2800/805* (2013.01)

(58) Field of Classification Search
CPC ......... A61K 8/988; A61K 35/644; A61K 8/37
See application file for complete search history.

(56) References Cited

U.S. PATENT DOCUMENTS

| 6,447,788 B1 | 9/2002 | Strathausen |
| 2007/0269400 A1 | 11/2007 | Golz-Berner et al. |
| 2011/0076376 A1* | 3/2011 | Montenegro Rizzardini .............. A23B 4/20 426/542 |
| 2011/0262551 A1 | 10/2011 | Nizard et al. |

FOREIGN PATENT DOCUMENTS

| AU | 201400060 A4 | 2/2014 | |
| EP | 1852017 A1 | 11/2007 | |
| FR | 2955770 A1 | 8/2011 | |
| JP | 2003093488 A * | 4/2003 | |
| KR | 20050048287 A * | 5/2005 | |
| KR | 20100010316 A1 | 2/2010 | |
| KR | 20100078777 A * | 7/2010 | |
| WO | 2010/082846 A1 | 7/2010 | |
| WO | 2011057421 A2 | 5/2011 | |
| WO | WO-2013061816 A1 * | 5/2013 | ........... C07H 15/203 |

OTHER PUBLICATIONS

Fischer-Rizzi, S. "Honey" from Complete Aromatherapy Handbook: Essential oils for radiant health, p. 202 (1 page) (Year: 1990).*
Syazana et al. BMC Complementary and Alternative Medicine 11:82. 9 pages. (Year: 2011).*
Ahmed et al. Malays J Med Sci.May 20(3): 6-13. (Year: 2013).*
Remington. Remington's Pharmaceutical Sciences. Gennaro, A., Ed. pp. 37, 1480, 1492, 144, 1498, 1513, 1516-1517. (Year: 1985).*
U1) Cosmetics info: Honey. Internet Archive date: Sep. 2, 2013. [Retrieved from the Internet on: Jun. 8, 2018]. Retrieved from: <URL: https://web.archive.org/web/20130902142701/http://www.cosmeticsinfo.org/ingredient/honey-0>.*
Jones et al. "The use of ETOH for the dilution of honey". Grana. 43(3), 174-182. (Year: 2004).*
U1) Sagovia, D. "The Clinical Benefits of Active Leptospermum Honey in Oncologic Wounds" from Wound Management and Prevention. vol. 56—Issue 10—Oct. 2010. (Year: 2010).*
(V1) Russell et al. J. Agric. Food Chem. 1990, 38, 10-13 (Year: 1990).*
Zaghloul et al. "Honey, a prospective antibiotic: extraction, formulation, and stability," Pharmazie. 2001. vol. 56, No. 8, pp. 643-647.
Mohapatia et al. "Antibacterial Efficacy of Raw and Processed Honey," Biotechnology Research International, vol. 2011, 6 pages, 2011.
Pyrzynska et al. "Analysis of phenolic acids and flavonoids in honey," Trends in Analytical Chemistry, vol. 28 No. 7, 2009 pp. 893-902.
Siess et al. "Flavonoids of Honey and Propolis: Characterization and Effects on Hepatic Drug-Metabolizing Enzymes and Benzo[α]pyrene-DNA Binding in Rats," J. Agric Food Chem., 44: 2297-2301 (1996).
Burlando et al., "Honey in dermatology and skin care: a review," *Journal of Cosmetic Dermatology* 12:306-313, 2013.
Kaškonienė et al., "Floral Markers in Honey of Various Botanical and Geographic Origins: A Review," *Comprehensive Reviews in Food Science and Food Safety* 9:620-634, 2010.
Molan, "Why honey is effective as a medicine," Bee World 82(1):22-40, 2001. (20 pages).
Skin Doctors Cosmeceuticals, "beetox 50ml," Product Information, URL=https://www.skindoctors.com.au/beetox-50ml/, download date Aug. 15, 2019, 4 pages.

(Continued)

*Primary Examiner* — Amy L Clark
(74) *Attorney, Agent, or Firm* — Seed IP Law Group LLP

(57) ABSTRACT

A cosmetic skin care product comprising a therapeutically effective amount of a honey extract is described, the honey extract having a phenolic compound to saccharides ratio of at least 5 times greater than the raw honey from which the extract is derived and including a mixture of at least ethanol, water and one or more MMP inhibitory phenolic compounds.

8 Claims, 4 Drawing Sheets

(56) References Cited

OTHER PUBLICATIONS

Skin Foods, "Light Moisturiser," Mintel GNPD Database Accession No. 666895, Mar. 2007, 1 page.
Skin Foods, "Light Moisturiser," Product Information, URL=https://www.skinfood.co.nz/shop/moisturiser/light-moisturiser, download date Aug. 15, 2019, 5 pages.
Weston et al., "Identification and quantitative levels of antibacterial components of some New Zealand honeys," *Food Chemistry* 70:427-435, 2000.

* cited by examiner

MATRIX-METALLOPROTEINASE (MMP) INHIBITORY EXTRACT AND METHODS OF USE THEREOF

TECHNICAL FIELD

Described herein is matrix-metalloproteinase (MMP) inhibitory extract and methods of use thereof. More specifically, an extract derived from honey is described as well as uses of this extract in the inhibition of MMP activity in cosmetic skin care products.

BACKGROUND ART

Honey is a well known active ingredient in many products including use in culinary applications, topical medical treatments including incorporation into existing cosmetic skin care formulations. Cosmetic skin care formulations often may not have sufficient honey included to confer any activity or if present, or the type of honey chosen only provides a low level if any of MMP inhibition. This is because honey at higher concentrations leads to formulation issues such as stickiness and high viscosity form the honey plus the inventors have found that only certain honey types confer MMP inhibition.

Matrix-metalloproteinases (MMP's) play an important role in skin aging. Activated by ultra-violet radiation (UV), an overexpression of MMPs can lead to a breakdown of collagen in the skin. This in consequence can cause reduced skin elasticity and the formation of wrinkles. MMP inhibitors are useful ingredients in anti-aging skin care formulations as they reduce photo-aging of the skin caused by collagen degradation. Natural MMP inhibitors have recently gained favour in the market.

The inventors have found that some honeys, for example manuka honey, can have MMP inhibition effects. Manuka honey is derived from the plant species *Leptospermum scoparium* and contains a wide range of phenolic and flavonoid compounds some of which have been identified and others remain as yet unknown. The exact activities of the various phenolics and flavonoids is still an area of rich research with many new compounds being identified and the activities elucidated. Manuka honey is a particularly well known honey for it's non-peroxide effects thanks in part to acceptance into topical medical applications and in particular, the anti-bacterial effects of methyl glyoxal (MGO) in this honey. Other *Leptospermum* genus honeys also have similar anti-bacterial effects linked with MGO such as *Leptospermum subtenue* and *Leptospermum polygalifolium*. In addition to the *Leptospermum* genus honeys, further honeys derived from *Kunzea* and *Knightia* genus such as kanuka (*Kunzea ericoides*) and rewarewa (*Knightia excelsa*) honeys also have high levels of phenolic and flavonoid concentrations. These honeys do not contain MGO but nevertheless show promise in having other forms of activity in vivo.

According to the inventor's work and knowledge, the phenolic component of honey appears to be the main component responsible for MMP inhibitory effects. Whilst the exact phenolic compounds conferring the activity are not known, the inventors have identified that phenolic extracts have this activity.

Methylsyringate (although itself not active) is a basic building block of many phenolic compounds. It can be measured easily (for example via HPLC) and is found in phenolic rich honeys. Methyl syringate can be found in existing commercialized skin care formulations in concentrations ranging from 8 to 40 μg/mL and by inference, a range of methyl syringate related phenolic compounds are also present in these products. In any case, the presence and extent of MMP inhibition effects appear to correlate to the concentration of methyl syringate in the extract.

While honey has useful MMP inhibitory effects as identified by the inventor's, honey does present a significant challenge when formulating skin care products. On the one hand, the formulator wants to maximize the concentration of honey in the formulation in order to maximize the MMP inhibition activity. On the other hand, even at low concentrations of 5% (w/w), the sugars in the honey can prove troublesome in skin care formulations. The sugars can cause an unpleasant, sticky skin feel and there can be issues with skin absorbtion. This therefore limits the concentration of honey possible and hence limits the activity of the final product.

To achieve a useful MMP inhibiting effect with honey, unpleasantly high sugar concentrations have to be introduced into the skin care formulation potentially rendering the product unmarketable due to poor cosmetic properties.

It should be appreciated that it would be useful to increase the MMP inhibitory effects of a skin care formulation whilst also avoiding the negative effects of honey in the formulation or at least to provide the public with a choice.

Further aspects and advantages of the extract and methods of use will become apparent from the ensuing description that is given by way of example only.

SUMMARY

Described herein is an MMP inhibitory extract and methods of use thereof. More specifically, an extract derived from honey is described as well as uses of this extract in the inhibition of matrix-metalloproteinase (MMP) activity and related skin care products. The extract allows for the inclusion of much greater concentrations of phenolics and hence much higher MMP inhibitory effects whilst avoiding formulating issues inherent to use of untreated honey.

In a first aspect, there is provided a cosmetic skin care product comprising a therapeutically effective amount of a honey extract, the honey extract having a phenolic compounds to saccharides ratio of at least 5 times greater than the raw honey from which the extract is derived and including a mixture of at least ethanol, water and one or more MMP inhibitory phenolic compounds.

In a second aspect, there is provided the use of a therapeutically effective amount of honey extract in the manufacture of a cosmetic skin care product to inhibit MMP activity on or in the skin of a subject to whom the cosmetic product is applied, wherein the cosmetic skin care product contains a honey extract, the honey extract having a phenolic compounds to saccharides ratio of at least 5 times greater than the raw honey from which the extract is derived and including a mixture of at least ethanol, water and one or more MMP inhibitory phenolic compounds.

In a third aspect, there is provided a method of treatment of a cosmetic skin condition by topical application of a cosmetic skin care product to the skin of a subject, wherein the cosmetic skin care product acts to inhibit skin MMP activity and wherein the cosmetic skin care product contains a therapeutically effective amount of a honey extract, the honey extract having a phenolic compounds to saccharides ratio of at least 5 times greater than the raw honey from which the extract is derived and including a mixture of at least ethanol, water and one or more MMP inhibitory phenolic compounds.

In a fourth aspect, there is provided a method of producing an MMP inhibiting honey extract including the steps of:
(a) mixing a selected honey with ethanol;
(b) separating the mixture to substantially remove a saccharide concentrated first phase from a second phase including ethanol, water and one or more MMP inhibitory phenolic compounds;
(c) conducting a further separation step to increase the phenolic compound concentration by reducing the ethanol and/or water concentration;
(d) collecting the resulting phenolic compound concentrate.

As should be apparent, the above extract, product, uses and methods allow the ability to include a far greater concentration of MMP inhibiting compounds in cosmetic skin care products than is possible with pure honey. As noted above, pure honey when used in skin care products confers unwanted characteristics to the product. By concentrating the MMP inhibiting compounds, it is possible to use far higher concentrations of these compounds than is the case with pure honey and this also avoids formulating issues. The extraction product and method also have some additional advantages namely, stabilization and preservation of the phenolics and transdermal enhancing features. The result is an enhanced value product with better efficacy in combination with improved stability, handling and use properties.

BRIEF DESCRIPTION OF THE DRAWINGS

Further aspects of the MMP inhibitory extract and methods of use thereof will become apparent from the following description that is given by way of example only and with reference to the accompanying drawing in which.

DETAILED DESCRIPTION

Figure 1:
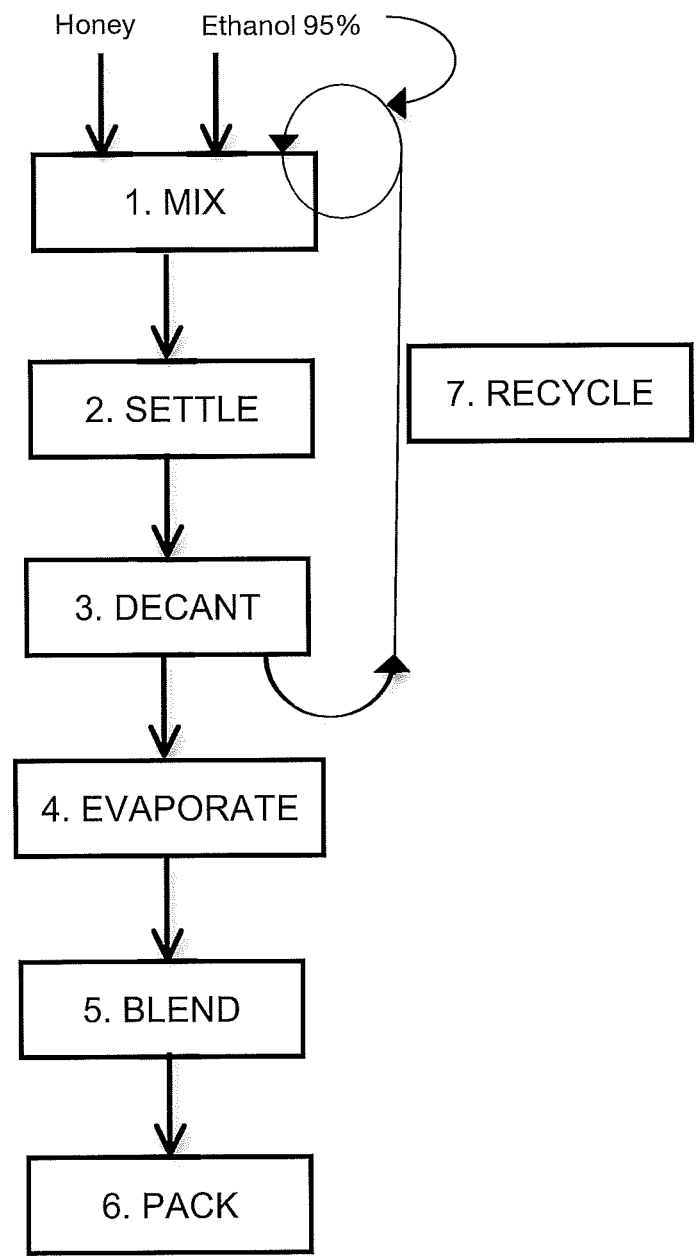
FIG. 1 illustrates a flow sheet of one method of producing the extract described herein.

As noted above, an MMP inhibitory extract and methods of use thereof are described. More specifically, an extract derived from honey is described as well as uses of this extract in the inhibition of matrix-metalloproteinase (MMP) activity and related skin care products. The extract allows for the inclusion of much greater concentrations of phenolics and hence much higher MMP inhibitory effects whilst avoiding formulating issues inherent to use of untreated honey.

For the purposes of this specification, the term 'about' or 'approximately' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'substantially' or grammatical variations thereof refers to at least about 50%, for example 75%, 85%, 95% or 98%.

The term 'comprise' and grammatical variations thereof shall have an inclusive meaning—i.e. that it will be taken to mean an inclusion of not only the listed components it directly references, but also other non-specified components or elements.

The term 'skin care product' or grammatical variations thereof refers to topically applied formulations for cosmetic use.

The term 'cosmetic' or grammatical variations thereof refers to compositions that may be applied to the human body for cleansing, beautifying, promoting attractiveness, or altering the appearance of wrinkles.

The term 'therapeutically effective amount' or grammatical variations thereof, with reference to an amount or dosage of a composition described herein, refers to an amount of a composition that is sufficient to cause a cosmetic effect.

The term 'honey' or grammatical variations thereof refers to a sweet and viscous fluid produced by honeybees and other insects from the nectar of flowers.

The terms 'pure honey' or 'unextracted honey' or 'raw honey' or grammatical variations thereof as used herein refer to a honey that has been produced by bees. Normal processing steps may have occurred such as water removal or reduction, filtration of the honey by up to 50 micron and/or sterilization, for example via irradiation.

The term 'honey substantially derived from' in reference to a specific genus or species of plant refers to honey produced from nectar, at least about 50%, or 75%, or 85%, or 95% or 98%, of which is derived from the species noted.

The term 'extract' and grammatical variations thereof as used herein refers to honey with at least a substantial proportion of naturally present sugars or saccharides having been removed form the pure honey.

The term 'phenolic compound' or grammatical variations as used herein refers to compounds including the base phenol structure:

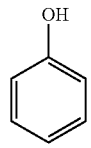

The phenolic compounds referred to herein may be simple phenols or polyphenolics.

The term 'MMP inhibition' or grammatical variations thereof refers to compounds that inhibit matrix metalloproteinase (MMP) activity in vivo. MMP activity may be completely stopped (full inhibition) or reduced to at least some extent dependent on the concentration of MMP inhibitors present as well as the relative inhibitory strength of the inhibitory compounds present.

In a first aspect, there is provided a cosmetic skin care product comprising a therapeutically effective amount of a honey extract, the honey extract having a phenolic compounds to saccharides ratio of at least 5 times greater than the raw honey from which the extract is derived and including a mixture of at least ethanol, water and one or more MMP inhibitory phenolic compounds.

The extract above may have a phenolic compounds to saccharides ratio of approximately 5, or 6, or 7, or 8, or 9, or 10, or 11, or 12, or 13, or 14, or 15, or 16, or 17, or 18, or 19, 20, or more times greater than the raw honey form which the extract is derived. In one embodiment, the extract may have a phenolic compound to saccharides ratio approximately 10-20 times greater than the raw honey. In another embodiment the extract may have a phenolic compound to saccharides ratio approximately 15 times greater than the raw honey.

The extract above may have a concentration of methyl syringate approximately 5, or 6, or 7, or 8, or 9, or 10, or 11, or 12, or 13, or 14, or 15, or 16, or 17, or 18, or 19, or 20 times higher than the concentration of methyl syringate in the raw honey. In one embodiment, the extract may have a concentration approximately 10-20 times more methyl syringate than the raw honey. In another embodiment, the extract may have a concentration approximately 15 times more methyl syringate than the raw honey. It should be appreciated that methyl syringate is not an MMP inhibitory compound itself however; this compound is easy to measure and provides a repeatable and reliable measure of general MMP inhibitory phenolic concentration. In fact, according to the inventor's work, the degree of MMP inhibitory effects correlates well with the concentration of methyl syringate in the extract. The result is that methyl syringate can provide a useful method of measuring MMP inhibition. Measurement may be completed via various known methods including, for example, via high performance liquid chromatography (HPLC).

The extract may contain approximately 200, or 300, or 400, or 500, or 600, or 700, or 800, or 900, or 1000 µg/mL of methyl syringate. In one embodiment, the extract may contain 200 to 1000 µg/mL of methyl syringate. As may be appreciated, this level of methyl syringate is greatly increased over that typically measured in honey or skin care products. By way of illustration one commercially available skin care product includes only 8 to 40 µg/mL of methyl syringate (and by inference similarly low other phenolic concentrations) compared to the extract noted above.

As noted above, methyl syringate is a simple phenolic compound form which many other phenolic compounds are derived. The exact phenolic compound(s) responsible for the observed MMP inhibition are not specifically known however, by way of illustration, honey contains many phenolics some of which are demonstrated in the table below:

Apigenin 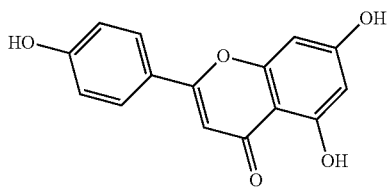 [SMILES: O=c1cc(-c2ccc(O)cc2)oc2cc(O)cc(O)c12]

Caffeic acid 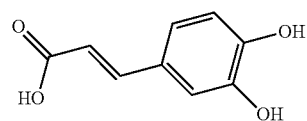 [SMILES: O=C(O)/C=C/c1ccc(O)c(O)c1]

Chlorogenic acid 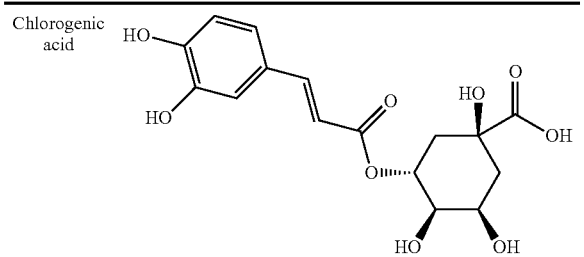

Chrysin 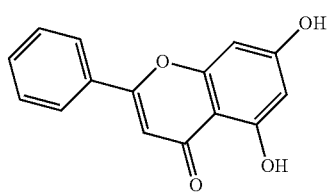 [SMILES: O=c1cc(-c2ccccc2)oc2cc(O)cc(O)c12]

Coumaric acid 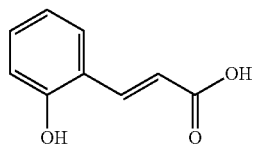 [SMILES: O=C(O)/C=C/c1ccccc1O]

Ellagic acid 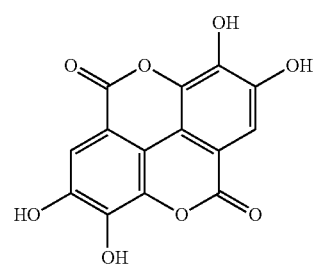 [SMILES: O=c1oc2c(O)c(O)cc3c(=O)oc4c(O)c(O)cc1c4c23]

Ferulic acid 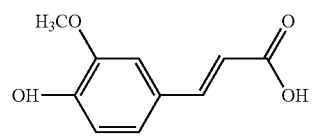 [SMILES: COc1cc(/C=C/C(=O)O)ccc1O]

Galangin 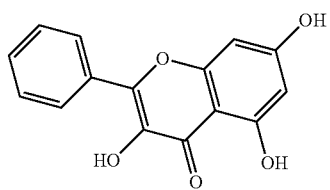 [SMILES: O=c1c(O)c(-c2ccccc2)oc2cc(O)cc(O)c12]

Gallic acid 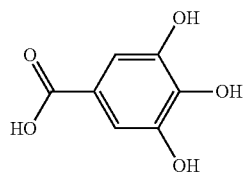

Kaempferol 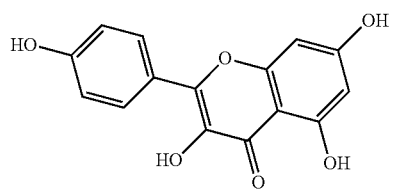 [SMILES: O=c1c(O)c(-c2ccc(O)cc2)oc2cc(O)cc(O)c12]

-continued

Myricetin
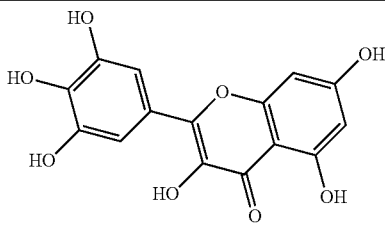

Luteolin
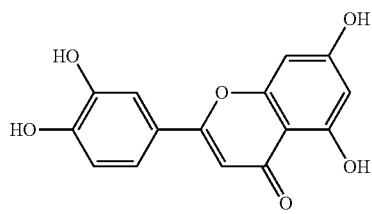 [SMILES: O=c1cc(-c2ccc(O)c(O)c2)oc2cc(O)cc(O)c12]

Pinocembrin
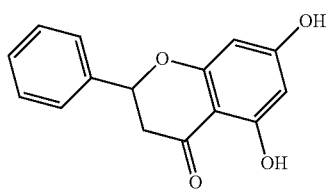 [SMILES: O=C1CC(c2ccccc2)Oc2cc(O)cc(O)c21]

Quercetin
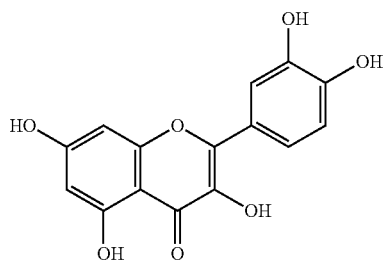 [SMILES: O=c1c(O)c(-c2ccc(O)c(O)c2)oc2cc(O)cc(O)c12]

Syringic acid
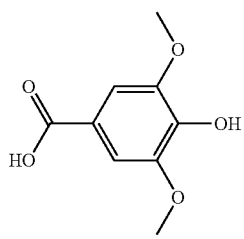

As may be appreciated, the actual active phenolic compound may be any one of these or may be a synergy of these or even other compounds.

The MMP's inhibited may be MMP-1 (collagenase-1), MMP-2 (gelatinase-A) and MMP-9 (gelatinase-B).

The degree of inhibition as measured based on 0.5% phenolics in the honey extract may be at least 10%. It should be appreciated that the measured degree of inhibition in the cosmetic skin care product may vary depending on the concentration of phenolics in the product and their floral origin and this figure is provided by way of illustration only.

The extract prior to formulation in the skin care product may contain approximately 10, or 15, or 20, or 25, or 30, or 35, or 40, or 45, or 50, or 55, or 60, or 65, or 70, or 75, or 80% ethanol. In one embodiment the extract may contain approximately 50 to 70% ethanol. It should be appreciated that this amount is provided by way of illustration however, the actual amount of ethanol may vary significantly depending on the amount of ethanol separation completed (e.g. via evaporation or distillation) and various other parameters such as the desired amount of ethanol wanted in the extract to assist further formulation work. The inventor's have found that retaining ethanol in the extract may be important and beneficial to aid with (a) phenolic stability during storage before formulation; (b) to act as a preservative and avoid microbial growth and (c) ethanol assists with transdermal penetration of the phenolics when formulated. More specifically, the phenolic compounds extracted are understood at least in part to be immiscible in water. The presence of ethanol in the extract means that the phenolic compounds remain in solution and avoids precipitation issues and hence instability and separation. Secondly, ethanol acts as a preservative preventing or at least limiting the growth of microbes in the solution. Both the stabilization and preservation characteristics of ethanol in this application mean that the extract can be stored for a considerable period of time prior to formulation as a skin care product. The last advantage of ethanol is that phenolics in the ethanol will be more readily absorbed into the skin since ethanol is a transdermal enhancer. Having the phenolics in a ready state for application makes formulation easier and avoids or at least minimizes the need to add additional transdermal agents. From a marketing and commercial perspective, ethanol may also be also be advantageous as a solvent since ethanol can be manufactured or obtained from natural processing methods and is well known and used in industry.

The extract prior to formulation in the skin care product may contain approximately 0.1, or 0.5, or 1, or 2, or 3, or 4, or 5, or 6, or 7, or 8, or 9, or 10, or 11, or 12, or 13, or 14, or 15, or 16, or 17, or 18% water. In one embodiment the extract may contain approximately 5 to 15% water. In one embodiment, the extract may contain 8 to 12% water. As may be appreciated, honey inherently contains up to 18% water naturally and the water in the extract may be that retrieved from the honey itself and not added by any other means.

The skin care product may contain approximately 0.1, or 0.2, or 0.3, or 0.4, or 0.5, or 0.6, or 0.7, or 0.8, or 0.9, or 1, or 2, or 3, or 4, or 5, or 6, or 7, or 8, or 9, or 10, or 11, or 12, or 13, or 14, or 15, or 16, or 17, or 18, or 19, or 20% (w/w) of extract. In one embodiment, the skin care product may contain approximately 1 to 5% extract. By way of comparison, approximately 2% extract in a skin care product gives an MMP inhibitory effect equivalent to that of a 30% pure honey concentration. This level of honey in a skin care product would be entirely unmanageable with many issues such as separation, stability, odour, a high viscosity and a high stickiness. All of these factors effectively render such as product unmarketable. By contrast, the skin care product noted above has none of the negative effects of pure honey and can be easily formulated (at 2% or even higher or lower as desired).

The cosmetic skin care product as described above may be formulated for topical administration as creams, gels, ointments, bars, lotions, or liquids. Specific product types include cleaners and toners, exfoliators and masks, moisturizers and lotions, and serums.

The honey from which the extract may be derived are those naturally rich in phenolic compounds. Examples may include honeys substantially derived from nectar produced by plants of the genus *Leptospermum, Kunzea* and *Knightia* and combinations thereof.

The *Leptospermum* genus plants may be those in the myrtle family Myrtaceae and may include: *Leptospermum scoparium, Leptospermum polygalifolium, Leptospermum subtenue, Leptospermum semibaccatum, leptospermum tri-*

*nervium, Leptospermum whitei, Leptospermum speciosum* and *Leptospermum liversidgei.*

The *Kunzea* genus plants may be those of the species *Kunzea ericoides* or kanuka tree.

The *Knightea* genus plants may be those of the species *Knightia excelsa* or rewarewa tree.

In a second aspect, there is provided the use of a therapeutically effective amount of honey extract in the manufacture of a cosmetic product to inhibit MMP activity on or in the skin of a subject to whom the cosmetic product is applied, wherein the cosmetic skin care product contains a honey extract, the honey extract having a phenolic compounds to saccharides ratio of at least 5 times greater than the raw honey from which the extract is derived and including a mixture of at least ethanol, water and one or more MMP inhibitory phenolic compounds.

In a third aspect, there is provided a method of treatment of a cosmetic skin condition by topical application of a cosmetic skin care product to the skin of a subject, wherein the cosmetic skin care product acts to inhibit skin MMP activity and wherein the cosmetic skin care product contains a therapeutically effective amount of a honey extract, the honey extract having a phenolic compounds to saccharides ratio of at least 5 times greater than the raw honey from which the extract is derived and including a mixture of at least ethanol, water and one or more MMP inhibitory phenolic compounds.

In the above method and use, the product may be used to cosmetically slow the visible signs of aging skin. MMP's are activated by ultra violet radiation (UV) and, as noted above, over expression of MMPs can lead to a break down of collagen in the skin leading to reduced skin elasticity and formation of wrinkles. The above method and use may be to increase skin elasticity, reduce photo aging of the skin and even influence skin wrinkles by reducing the length, depth and formation of wrinkles.

The cosmetic skin care product used may be applied once or twice daily depending on the final concentration and strength of the inhibitory compounds in the final product.

In a fourth aspect, there is provided a method of producing an MMP inhibiting honey extract including the steps of:
  (a) mixing a selected honey with ethanol;
  (b) separating the mixture to substantially remove a saccharide concentrated first phase from a second phase including ethanol, water and one or more MMP inhibitory phenolic compounds;
  (c) conducting a further separation step to increase the phenolic compound concentration by reducing the ethanol and/or water concentration;
  (d) collecting the resulting phenolic compound concentrate.

The ratio of honey to ethanol in step (a) may be approximately 1 to 10 parts honey to 10 to 1 part ethanol. The ratio may be approximately 1 part honey to 0.1, or 0.2, or 0.3, or 0.4, or 0.5, or 0.6, or 0.7, or 0.8, or 0.9, or 1.0, or 1, or 1.5, or 2.0, or 2.5, or 3.0, or 3.5, or 4.0, or 4.5, or 5, or 5.5, or 6.0, or 6.5, or 7.0, or 7.5, or 8.0, or 8.5, or 9.0, or 9.5, or 10 parts ethanol on weight basis. In one embodiment, the ratio may be approximately one part honey to one part ethanol or a 50:50 ratio by weight.

Mixing in step (a) may occur at a temperature of approximately 15, or 20, or 25, 30, or 35, or 40, or 45, or 50° C. In one embodiment, the temperature may be from 30 to 35° C. Mixing may occur in an agitated tank although other methods may be used. Lower temperatures (below 50° C.) are preferable so as to avoid unwanted degradation in activity of actives present in the extract. Higher temperatures also create handling issues with ethanol becoming highly volatile. Mixing may occur for at least 1 minute. Mixing may occur for 10 to 120 minutes. In one embodiment, mixing occurs until a uniform puree is formed.

After mixing in step (a) and prior to separating in step (b), the mixture may be allowed to settle into the two phases noted in step (b). Settling may for example involve stopping any agitation occurring and allowing the two phases to part via gravity. Settling may be encouraged by cooling the mixed solution, for example by passing coolant around the walls of the mixing tank. Settling may occur for at least 1 minute. In one embodiment, settling may take approximately 6 to 48 hours. In a further embodiment settling may take 1 to 2 weeks. As should be appreciated, there is no upper limit for this time period since the phenolic compounds post mixing are stabilized in the ethanol and separation can occur when processing constraints require further processing.

Separation in step (b) may occur by decanting one phase from the other. As may be appreciated, the saccharides removed may primarily be fructose and sucrose. The separated first saccharide or syrup phase may be recycled back into the first mixing step to recover further phenolics as desired noting that an optimum will be reached over time defining the limit of recycling being the point which the energy cost of recycling outweighs the potential extra gains in extracting the phenolics. It is understood that the ethanol concentration post decanting is approximately 70, or 75, or 80, or 85, or 90, or 95% (w/w). Some water (<18%) will also be present, the water being derived from what is present in the honey naturally.

Separation in step (c) may be via evaporation although other separation methods may be used such as via distillation. One evaporation means may be via use of a falling film evaporator and evaporation under vacuum. A vacuum in particular may be beneficial to avoid the need to elevate the temperature since higher temperatures may have an impact on the activity of the extracted phenolic compounds. As noted above, keeping the temperature lower is advantageous both to prevent potential harm to the active phenolic compounds and also to avoid ethanol handling issues. It is anticipated that some water may also be removed during the evaporation process.

Following separation in step (c), further processing may be undertaken to standardize the resulting extract. Standardizing steps may for example including blending of various extracts together to form a consistent amount of marker phenolic compound such as methyl syringate. As may be appreciated, honey being a so called natural product can produce varying concentrations of phenolic compound depending on many factors such as floral origin, geographical origin and floral purity. Blending may be a way to achieve a consistent extract activity for further use in products such as cosmetic skin care products.

In addition to standardization, the final extract may be packaged prior to further processing. Packaging may be useful for handling and storage. Packaging may also be important to ensure storage stability.

The extract may have a specific gravity below that of water. In one embodiment the specific gravity may be approximately 0.9 to 0.999. The specific gravity might be approximately 0.990.

The extract may be acidic. In one embodiment, the pH may be from approximately 3.0 to 6.0. The pH may be approximately 4.0 to 5.0.

The extract may have a solids content post extraction of approximately 0.1% to 99.9% w/w, or up to as high as the extraction process will allow. In one embodiment the solids content may be approximately 30 to 40% w/w. In another embodiment the solids content may be 50 to 60% w/w. In a further embodiment the solids content may be 60 to 75%. In a still further embodiment the solids content may be 75 to 85%. Solids may be residual sugars, bee proteins, wax particles and environmental dust, all being typical solids found in honey. As should be appreciated, honeys finely filtered before under going the above extraction process may have fewer solids while unfiltered honeys may have solids at the higher end of the range noted.

The extract may be further characterized by having a honey aromatic odour and a golden yellow colour.

It is anticipated that the extract may have a shelf life of at least 24 months provided it is stored in a cool and dry area and shielded from UV light.

It should further be noted that reference has been made above to the presence of phenolic compounds in the extract. As may be appreciated, honey also contains flavonoid compounds and it is the inventor's understanding the flavonoid compounds may also be present in the extract and skin care product.

As should be apparent, the above extract, product, uses and methods allow the ability to include a far greater concentration of MMP inhibiting compounds in cosmetic skin care products than is possible with pure honey. As noted above, pure honey when used in skin care products confers unwanted characteristics to the product. By concentrating the MMP inhibiting compounds, it is possible to use far higher concentrations of these compounds than is the case with pure honey and this also avoids formulating issues. The extraction product and method also have some additional advantages namely, stabilization and preservation of the phenolics and transdermal enhancing features. The result is an enhanced value product with better efficacy in combination with improved stability, handling and use properties.

The embodiments described above may also be said broadly to consist in the parts, elements and features referred to or indicated in the specification of the application, individually or collectively, and any or all combinations of any two or more said parts, elements or features, and where specific integers are mentioned herein which have known equivalents in the art to which the embodiments relates, such known equivalents are deemed to be incorporated herein as of individually set forth, Where specific integers are mentioned herein which have known equivalents in the art to which this invention relates, such known equivalents are deemed to be incorporated herein as if individually set forth.

WORKING EXAMPLES

The above described MMP inhibitory extract and methods of use are now described by reference to specific examples.

Example 1

An example method of producing an extract is described.

Referring to FIG. 1, honey is selected and mixed with ethanol in item 1 termed 'mix'.

The honey may be a honey known to have greater concentrations of phenolic and flavonoid compounds such as those derived from the genus *Leptospermum, Kunzea* and *Knightia*. The ethanol may be 95% pure (absolute ethanol). The honey and ethanol may be added at a 50:50 rate i.e. at equal weights, until the desired volume is reached. The mixing process may be completed in an insulated tank at a temperature of 30-35° C. for 30 to 60 minutes or until a smooth puree is formed.

Post mixing (item 1) and settling (item 2), the result is two phases of solution, the upper layer being a syrup formed primarily from the saccharides from the honey such as fructose and sucrose. The lower layer is a mixture of ethanol, water extracted from the honey (typically 0-18%), and the phenolic compounds. Settling and separation may be enhanced by cooling the mixture for example via coolant pumped around the tank walls. Settling may take approximately 24 hours although this time period is variable depending on operator preference. Whilst in this state, the phenolic compounds are stable.

In item 3, decanting, the upper saccharide rich layer is decanted off to leave the ethanol mixture. The separated saccharide portion may be recycled (item 7) back into mixing (item 1) to maximize separation of the phenolics.

In item 4, evaporation, the phenolics are concentrated by removing ethanol and/or water via an evaporation process. One evaporator processing unit may be a falling film evaporator.

Evaporation may be completed under vacuum conditions in order to minimize the use of heat and possible damage to active compounds. Other separation methods may be used such as distillation.

Items 5 and 6 are finishing steps that may optionally be undertaken. Blending in item 5 refers to steps that might be completed to ensure a consistent or standardized product quality is achieved—for example blending of the product with other extracts to achieve a consistent and measurable level of phenolics in the final extract. Item 6, packing, may be complete for ease of handing and storage as well as to stabilize the extract during storage.

Example 2

A known honey extract composition and anticipated ranges for the various characteristics of the composition is illustrated in Table 1 below.

TABLE 1

| Honey Extract | | |
|---|---|---|
| Extract Characteristic | Formulation 1 | Envisaged Formulation Characteristic Ranges |
| Odour | Honey, aromatic | Honey, aromatic |
| Colour | Golden yellow | Golden yellow |
| Ethanol Concentration | 64% | 50 to 80% (v/v) |
| Water Concentration | 10% | 5 to 40% |
| Specific Gravity/20° C. (g/ml) | 0.990 | |
| pH | 4.60 | 4 to 5 |
| Total Solids | 34.9% | 20 to 85% |
| Methyl Syringate concentration (µg/mL) | 200-1000 | 200 to 1000 |

Example 3

The above extract was tested in skin care formulation base creams and rinses. Given the extract contains at least 15 fold higher concentration phenolic compounds than the raw honey, a relatively low concentration of honey extract, for example 1-4% (w/w) concentration equates to an equivalent honey concentration of 15-100% (w/w) in the skin care formulation.

Some more specific formulations are demonstrated below in Table 2.

TABLE 2

Example Cosmetic Skin Care Formulations

| Compound | Cosmetic Product | | | |
|---|---|---|---|---|
| | Day Moisturiser | Night Moisturiser | Facial Serum | Hydrating Facial Mask |
| Water | 50-70% | 60-70% | 50-60% | 50-70% |
| Emollients | 10-15% | 15-20% | — | 15-20% |
| Emulsifier | 4-6% | 6-7% | — | 4-6% |
| Stabiliser | 1-2% | 1-3% | 2-4% | 1-3% |
| Honey Extract | 1-2% | 1-2% | 4-6% | 2-4% |
| Other active ingredients (not honey extract related) | — | — | 10-15% | — |

In addition to the above, each product may also contain preservatives and/or fragrance.

As may be appreciated, a 15% or higher honey concentration would be entirely unworkable and sticky and of no commercial value. Cosmetic skin care products containing the honey extract are by contrast are very easy to formulate and provide a far higher MMP inhibition rate over that of existing products. An added advantage is that the residual ethanol in the extract assist in keeping the phenolics stable and minimizes microbial growth when stored prior to formulation with the extra skin care compounds. Ethanol may also act as a penetration enhancer assisting transfer of the phenolics into the skin. No unpleasant odour resulted from use of the extract as can be the case with honey.

Example 4

In this example, the MMP inhibitory effects of various honey extracts are illustrated in an in vitro experiment. The MMP inhibitory effects of the extracts were tested directly.

Assays were prepared for MMP-1, MMP-2 and MMP-9 and treated with extracts made by the method above from manuka honey, kanuka honey, a blend of manuka and kanuka honey and clover honey. Multiple concentrations of honey extract were used.

Figure 2:
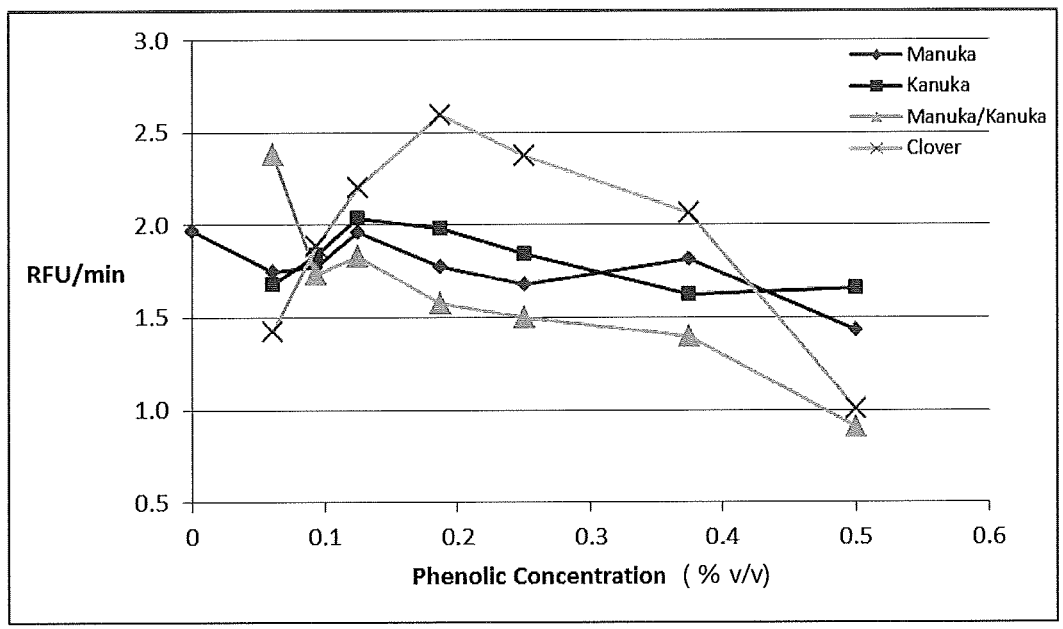
FIG. 2 is a graph illustrating the relationship between differing phenolic concentrations of different honeys and the activity of MMP-1.

As shown in FIG. 2, the relative fluorescence per minute (RFU/min) of each honey extract was tested with respect to MMP-1. The honeys rich in phenolic compounds (manuka, kanuka and manuka/kanuka blend) showed the greatest degree of inhibition while clover honey with few phenolic compounds had minimal MMP inhibitory effects. Normalizing the data against a 0.5% phenolic concentration, manuka honey was found to inhibit MMP-1 activity by 19.5%, kanuka honey inhibited MMP-1 by 13.5%, the manuka/kanuka blend inhibited by 58%. Clover honey had a significant variability to extent that the inhibition figures were not reliable.

Figure 3:
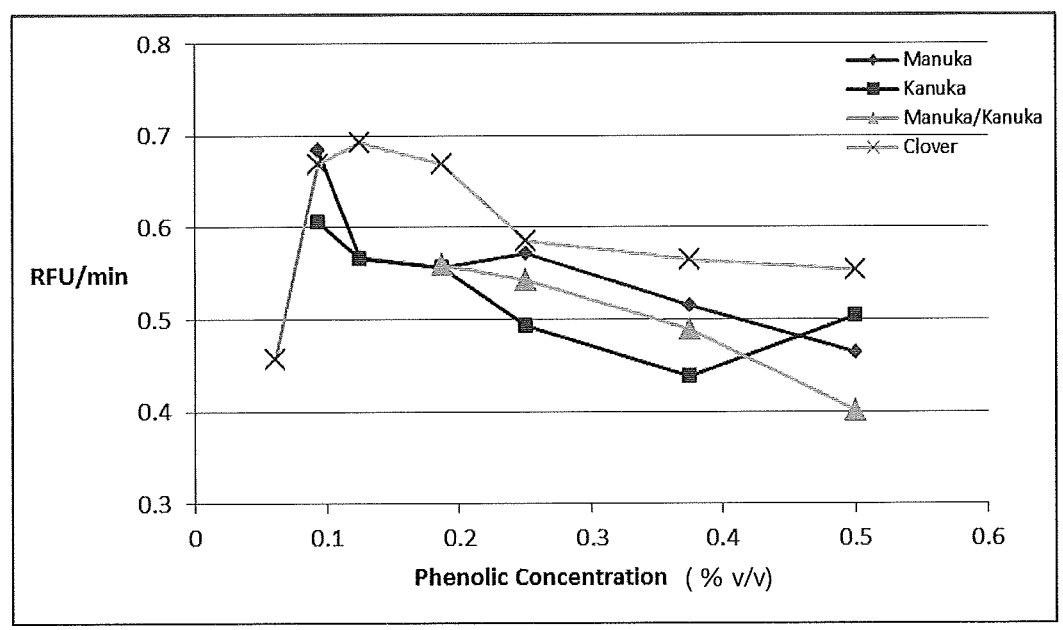
FIG. 3 is a graph illustrating the relationship between differing phenolic concentrations of different honeys and the activity of MMP-2.
Figure 4:
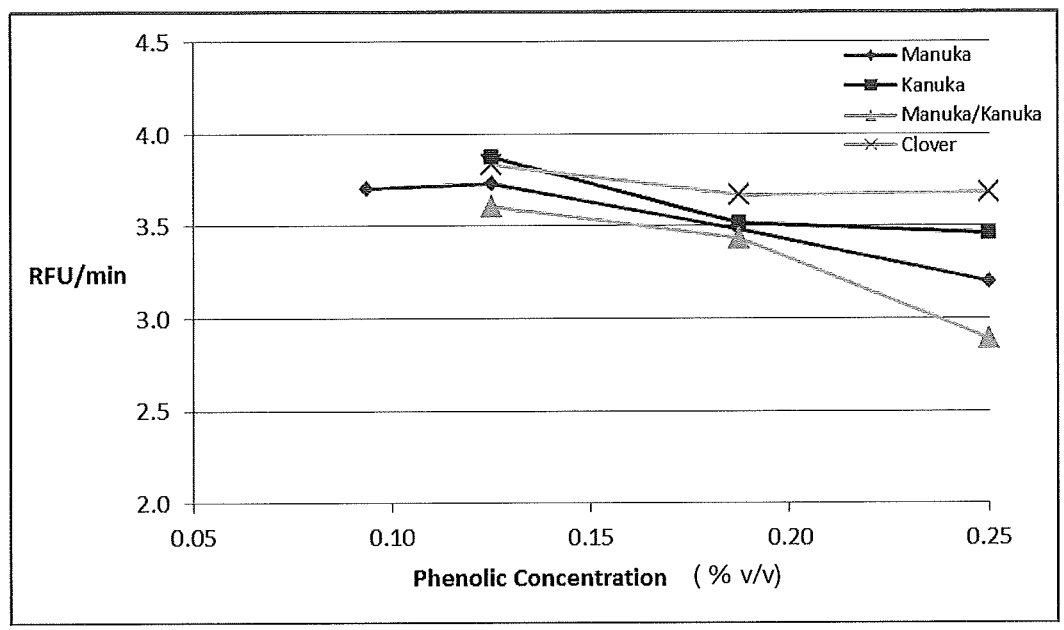
FIG. 4 is a graph illustrating the relationship between differing phenolic concentrations of different honeys and the activity of MMP-9.

FIGS. 3 and 4 illustrate the inhibitory effects of the honeys against MMP-2 and MMP-9 respectively.

All four honey extracts showed MMP-2 inhibition to some degree with the clover honey extract having the least effect. Clover honey again when normalized had too much variation to be reliable whilst the other honey extracts showed strong correlations. The normalized inhibitions based on 0.5% phenolics were manuka 69.5%; kanuka 24.0%, manuka/kanuka blend 76.0% and clover honey extract 8.5%.

The rates of MMP-9 inhibition were considerably higher than that from MMP-1 and MMP-2 inhibition. The same trends were noted for MMP-9 inhibition with the phenolic rich honeys have well correlated normalised results and inhibitions (for a 0.5% phenolic concentration, the results were manuka honey extract 39.5% inhibition; kanuka honey extract 13.0% inhibition; manuka/kanuka blend 82.0% inhibition and clover honey 9.0% inhibition.

Example 5

Figure 5:
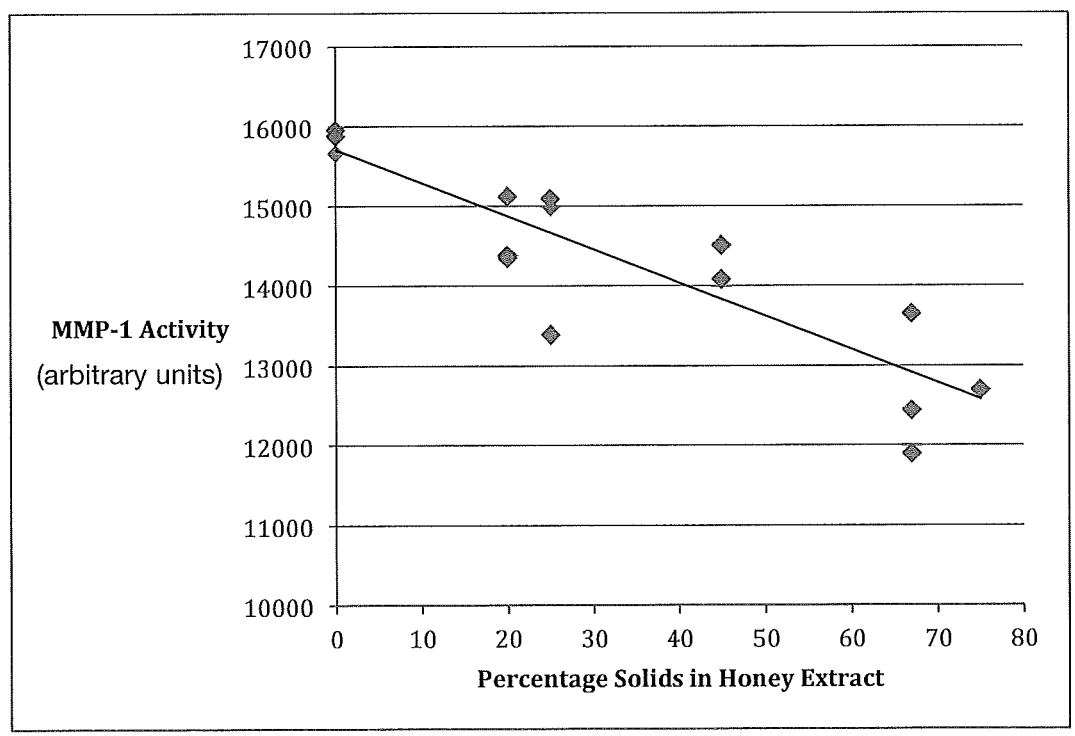
FIG. 5 is a graph illustrating the relationship between concentration of honey extract sample based on proportion of solids and the activity of MMP-1.

In this example, the MMP-1 inhibitory effects of differing concentrations (measured by solids proportion) of an extract were tested. After ethanol extraction, ethanol and some water were evaporated to obtain differing solids concentrations. The solids are mainly made up of sugars derived from the extracted honey. The samples were 20, 25, 45, 67 and 75% solids in the course of the evaporation. As shown in FIG. 5, MMP-1 inhibition increases at higher concentrations. The samples were also analyzed by HPLC to determine methyl syringate concentration, which were determined to be as follows. The sample with 0% solids was a control containing no honey extract:

| % Solids in Sample | Methyl Syringate Concentration (microgram/mL) |
|---|---|
| 0% | 0 |
| 0% | 0 |
| 0% | 0 |
| 20% | 3 |
| 20% | 3 |
| 20% | 3 |
| 25% | 2 |
| 25% | 2 |
| 25% | 2 |
| 45% | 30 |
| 45% | 30 |
| 45% | 30 |
| 67% | 259 |
| 67% | 259 |
| 67% | 259 |
| 75% | 238 |

Figure 6:
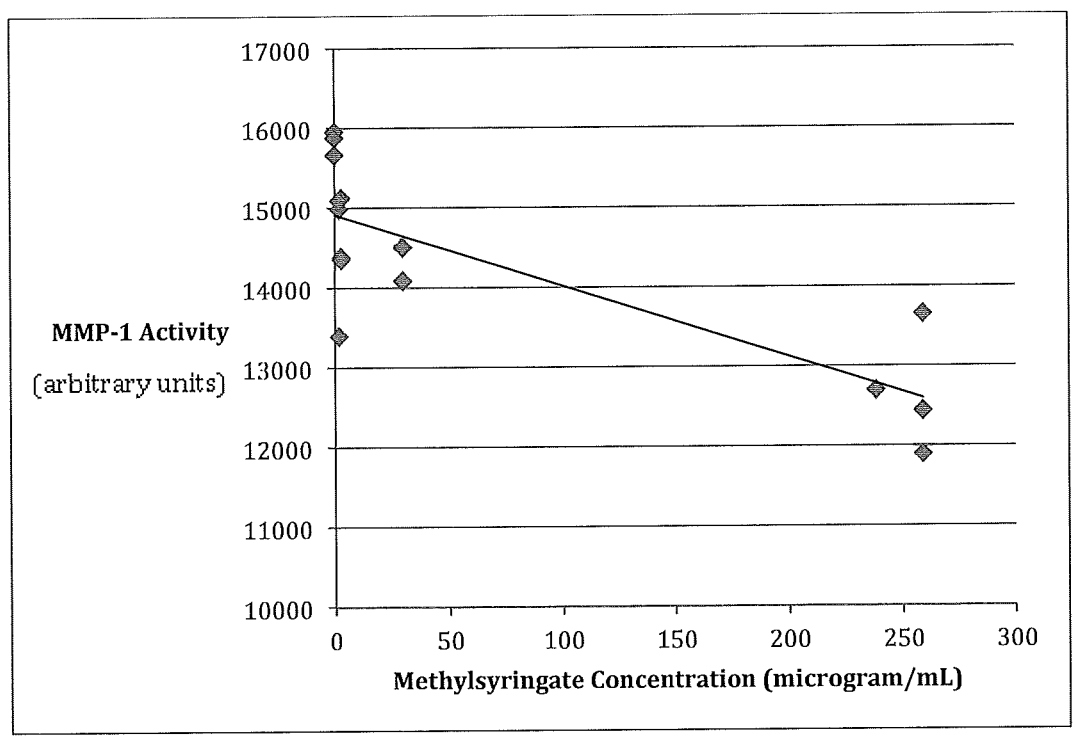
FIG. 6 is a graph illustrating the relationship between concentration of methylsyringate concentration and activity of MMP-1.

As shown in FIG. 6, higher methyl syringate concentrations show a greater degree of inhibition of MMP-1 activity. This illustrates the usefulness of methyl syringate as a marker compound for MMP inhibition.

Aspects of the MMP inhibitory extract and methods of use have been described by way of example only and it should be appreciated that modifications and additions may be made thereto without departing from the scope of the claims herein.

What is claimed is:

1. A skin care product for inhibiting skin aging, loss of skin elasticity or wrinkle formation, the skin care product comprising a therapeutically effective amount of a honey extract obtained from raw honey, wherein the honey extract comprises one or more MMP inhibitory phenolic compounds, between 200 to 1000 μg/mL of methyl syringate, ethanol, and water, and wherein the ethanol is present in an amount effective to stabilize the one or more MMP inhibitory phenolic compounds and to preserve the extract, the amount of methyl syringate in the extract is approximately 5 to 20 times higher than in raw honey, the extract has a ratio of one or more MMP inhibitory phenolic compounds to saccharides that is at least 5 times greater than in the raw honey, and wherein the raw honey from which the extract is obtained is substantially from nectar produced by plants of the genus *Leptospermum, Kunzea, Knightia*, or a combination thereof.

2. The skin care product as claimed in claim 1, wherein the honey extract contains 10-80% ethanol.

3. The skin care product as claimed in claim 1, wherein the honey extract contains 0.1-18% water.

4. The skin care product as claimed in claim 1, wherein the skin care product contains 0.1 to 20% (w/w) of the honey extract.

5. The skin care product as claimed in claim 1, wherein the skin care product further comprises an emollient or an emulsifier, and wherein the skin care product is formulated for topical administration in the form of a cream, gel, ointment, bar, lotion, or liquid.

6. A therapeutically effective honey extract obtained by:
   mixing raw honey with ethanol to provide a mixture;
   separating the mixture to substantially remove a saccharide concentrated first phase from a second phase including one or more MMP inhibitory phenolic compounds, ethanol, water and methyl syringate;
   conducting a further separation step to increase the concentration of the one or more MMP inhibitory phenolic compounds and methyl syringate by reducing the ethanol and/or water concentration to provide the honey extract; and
   collecting the honey extract, wherein the honey extract comprises one or more MMP inhibitory phenolic compounds, between 200 to 1000 µg/mL of methyl syringate, ethanol in an amount effective to stabilize the one or more MMP inhibitory phenolic compounds and to preserve the extract, and water, wherein the raw honey from which the extract is obtained is substantially-from nectar produced by plants of the genus *Leptospermum, Kunzea, Knightia*, or a combination thereof.

7. The skin care product as claimed in claim 1, wherein the honey extract contains 50-70% ethanol.

8. The skin care product as claimed in claim 1, wherein the honey extract contains at least 10% ethanol.

* * * * *